US005821312A

United States Patent [19]

Mandeville, III et al.

[11] Patent Number: 5,821,312
[45] Date of Patent: Oct. 13, 1998

[54] ACID-FUNCTIONALIZED SACCHARIDES AS POLYVALENT ANTI-INFECTIVES

[75] Inventors: W. Harry Mandeville, III, Lynnfield; Venkata R. Garigapati, Waltham, both of Mass.

[73] Assignee: GelTex Pharmaceuticals, Inc., Waltham, Mass.

[21] Appl. No.: 882,417

[22] Filed: Jun. 25, 1997

Related U.S. Application Data

[62] Division of Ser. No. 717,264, Sep. 20, 1996, Pat. No. 5,700,458.

[51] Int. Cl.$^6$ .......................... C08F 24/00; C08F 220/56; C08F 220/58

[52] U.S. Cl. ............................... 526/238.23; 526/303.1; 526/304; 526/266

[58] Field of Search ........................... 526/238.23, 266, 526/303.1, 304

[56] References Cited

U.S. PATENT DOCUMENTS

| 4,721,760 | 1/1988 | Graafland | 526/238.23 |
| 4,868,289 | 9/1989 | Magnusson et al. | 536/4.1 |
| 5,034,516 | 7/1991 | Roy et al. | 536/4.1 |

FOREIGN PATENT DOCUMENTS

91/08747  6/1991  WIPO.

OTHER PUBLICATIONS

Nakaya, T., et al., "Polymeric glycolipid analogues, 3$^{a)}$, Polymethacrylates containing glucose moieties attached to the polymer backbones via n–alkyl chains of various length," *Makromol. Chem., Rapid Commun.*, 14:77–83 (1993).

Roy, R., et al., "Synthesis of Antigenic Carbohydrate Polymers Recognized by Lectins and Antibodies," *J. Chem. Soc., Chem. Commun.*, pp. 1058–1060 (1988).

Mammen, M., et al., "Effective Inhibitors of Hemagglutination by Influenza Virus Synthesized from Polymers Having Active Ester Groups. Insight into Mechanism of Inhibition," *J. Med. Chem.*, 38:4179–4190 (1995).

Itoh, M., et al., "Suppression of Influenza Virus Infection by an N–Thioacetylneuraminic Acid Acrylamide Copolymer Resistant to Neuraminidase," *Virology*, 212:340–347 (1995).

Matrosovich, M.N., "Towards the development of antimicrobial drugs acting by inhibition of pathogen attachment to host cells: a need for polyvalency," *FEBS. LET*, 252(1, 2):1–4 (1989).

Sparks, M.A. et al., "Neuraminidase–Resistant Hemagglutination Inhibitors: Acrylamide Copolymers Containing a C–Glycoside of N–Acetylneuraminic Acid," *J. of Med. Chem.*, 36(6):778–783 (1993).

Spaltenstein, A. and Whitesides, G.M., "Polyacrylamides Bearing Pendant α–Sialoside Groups Strongly Inhibit Agglutination of Erythrocytes by Influenza Virus," *J. Am. Chem. Soc.*, 113:686–687 (1991).

Kingery–Wood, J.E. et al., "The Agglutination of Erythrocytes by Influenza Virus is Strongly Inhibited by Liposomes Incorporating an Analog of Sialyl Gangliosides," *J. Am. Chem. Soc.*, 114(18):7303–7305 (1992).

Matrosovich, M.N. et al., "Synthetic polymeric sialoside inhibitors of influenza virus receptor–binding activity," *FEBS LETTERS* 272(1,2):209–212 (Oct. 1990).

Byramova, N.E. et al., "Synthesis of Sialic Acid Pseudopolysaccharides by Coupling of Spacer–Connected Neu5Ac With Activated Polymer," *J. Carbohydrate Chem.*, 10(4):691–700 (1991).

Glass, R.I. et al., "Rotavirus Vaccines: Success by Reassortment?," *Science*, 265:1389–1391 (Sep. 1994).

Blacklow, N.R. and Greenberg, H.B., "Viral Gastroenteritis," *N. En. J. Med.*, 325:252–264 (Jul. 1991).

LeBaron, C.W. et al., "Annual Rotavirus Epidemic Patterns in North America," *J. Am. Med. Assoc.*, 264:983–988 (Aug. 1990).

Yolken, R.H. et al., "Sialic Acid Glycoproteins Inhibit In Vitro and In Vivo Replication of Rotaviruses," *J. Clin. Invest.*, 79:148–154 (Jan. 1987).

Kiefel, M.J. et al., "Synthesis and Biological Evaluation of N–Acetylneuraminic Acid–Based Rotavirus Inhibitors," *J. Med. Chem.* 39:1314–1320 (1996).

Yuen, C.–T. et al., "Novel Sulfated Ligands for the Cell Adhesion Molecule E–Selection Revealed by the Neoglycolipid Technology Among O–Linked Oligosaccharides on an Ovarian Cystadenoma Glycoprotein," *Biochemistry* 31:9126–9131 (1992).

Roy, R. et al., "Solid–phase Synthesis of Dendritic Sialoside Inhibitors of Influenza A Virus Haemagglutinin," *J. Chem. Soc., Chem. Commun.*:1869–1872 (1993).

Sigal, G.B. et al., "Polyacrylamides Bearing Pendant α–Sialoside Groups Strongly Inhibit Agglutination of Erythrocytes by Influenza Virus: The Strong Inhibition Reflects Enhanced Binding Through Cooperative Polyvalent Interactions," *J. Am. Chem. Society*, 118(6):3789–3800 (Apr. 1996).

(List continued on next page.)

*Primary Examiner*—Joseph L. Schofer
*Assistant Examiner*—Wu C. Cheng
*Attorney, Agent, or Firm*—Hamilton, Brook Smith & Reynolds, P.C.

[57] ABSTRACT

The present invention includes polymerizable monomers comprising an acid-functionalized glycoside moiety. The monomer can have a polymerizable functional group, such as an olefinic bond, to which the acid-functionalized glycoside moiety is attached by a spacer group, for example, an alkylene group, or an alkylene group wherein one or more carbon atoms are substituted by heteroatoms, such as oxygen, nitrogen or sulfur atoms. The present invention also includes polymers comprising pendant acid-functionalized glycoside moieties. The present invention also provides a method for treating a microbial infection in a mammal by administering to the mammal a therapeutically effective amount of a polymer comprising one or more acid-functionalized glycoside moieties.

10 Claims, No Drawings

OTHER PUBLICATIONS

Jain, R.K. et al., "Total Synthesis of 3'–O–Sialyl, 6'–O–Sulfo Lewis$^x$, NeuAca2→ 3(6–O–SO$_3$Na)Galβ1→ 4(Fucα1→)–GlcNAcβ–OMe: A Major Capping Group of GLYCAM–I," *J. Am. Chem. Soc.*, 116:12123–12124 (1994).

Lamblin, G. et al., "Structure of two sulphated oligosaccharides from respiratory mucins of a patient suffering from cystic fibrosis," *Biochem. J.*, 275:199–206 (1991).

Lubineau, A. and Lemoine, R., "Regioselective Sulfation of Galactose Derivatives Through the Stannylene Procedure. New Synthesis of the 3'–O–Sulfated Lewis$^a$ Trisaccharide," *Tetrahedron Letters*, 35 (47):8795–8796 (1994).

Chandrasekaran, E.V. et al., "Ovarian Cancer α1,3–L–Fucosyltransferase," *The J. of Biological Chem.*, 267(33):23806–23814 (Nov. 25, 1992).

Reddy, G.V. et al., "Synthesis of Precursors For the Dimeric 3–O–SO$_3$Na Lewis X and Lewis A Structures," *Carbohydrate Research*, 280:261–276 (1996).

Ohmoto, H., et al., "Studies on Selectin Blocker. 1. Structure–Activity Relationships of Sialyl Lewis X Analogs," *J. Med. Chem.*, 39:1339–1343 (1996).

Geyer, H. et al., "Oligosaccharide Pattern of HIV–2 gp120; Dependence on Host Cells and Virus Isolates," *Complex Carbohydrates in Biology and Medicine*, Abstract U104: p. 266.

Haynes, P.A. and Cross, G.A.M., "Studies On The Structure And Function Of A Novel Carbohydrate Antigen Of Trypanosoma Cruzi," *Complex Carbohydrates in Biology and Medicine*, Abstract U105: p. 266.

Oda, Y. et al., "Structure–Function Studies On Carbohydrate Ligands Of Three Selectins. Modifications To Fucose, Sialic Acid And Sulfate As A Sialic Acid Replacement," *Complex Carbohydrates in Biology and Medicine*, Abstract U106: p. 266.

Linn, P. et al., "Site Specific Chemical Modification Of A Strep–Tococcal Antibody Binding Site," *Complex Carbohydrates in Biology and Medicine*, Abstract U107:p.266.

Guilbert, B. et al., "Dibutylstannylene Acetals: Useful Intermediates for the Regioselective Sulfation of Glycosides," *Tetrahedron: Asymmetry*, 5(11):2163–2178 (1994).

Ragan, J.A. and Cooper, K., "Synthesis Of A Galactose–Fucose Disaccharide Mimic of Sialyl Lewis X," *Biorganic & Medicinal Chemistry Letters*, 4(21):2563–2566 (1994).

ACID-FUNCTIONALIZED SACCHARIDES AS POLYVALENT ANTI-INFECTIVES

RELATED APPLICATION

This application is a division of application Ser. No. 08/717,264 filed Sep. 20, 1996 now U.S. Pat. No. 5,700,458 which is incorporated herein by reference in its entirety.

BACKGROUND OF THE INVENTION

The infection of a host cell by a microbe, such as a virus, a bacterium or a protozoan, proceeds via initial attachment of the microbe to the host cell surface. This process is mediated by relatively weak attractive interactions between adhesion molecules on the surfaces of the microbe and the host cell. In general, microbe-host cell attachment is the product of a multiplicity of such interactions, via what has been referred to as the polyvalent effect. One well-studied example of such a process is the attachment of the influenza A virus to mammalian epithelial cells, which results from interaction of terminal N-acetylneuraminic acid groups of glycolipids and glycoproteins on the host cell surface with the attachment glycoprotein hemagglutinin on the viral surface.

The growing problem of bacterial resistance to conventional antibiotics and the paucity of effective antiviral agents both point to the need for new approaches to the treatment of microbial infections. The attachment step is an attractive target for such a treatment, and much activity has focused on the development of N-acetylneuraminic acid-containing compounds capable of binding to viral hemagglutinin, thus inhibiting viral attachment to host cells. Studies have demonstrated that polyvalent compounds, such as polymers bearing pendant N-acetylneuraminic acid groups, bind influenza virus with association constants which are several orders of magnitude higher than those of monomeric N-acetylneuraminic acid derivatives. To date, no polyvalent N-acetylneuraminic acid containing compounds are in clinical use for treatment or prevention of influenza.

A disadvantage of N-acetylneuraminic acid-functionalized compounds as therapeutic agents for the treatment of infection by influenza A virus and, possibly, other microbes, is the great expense of this sugar. In addition, the influenza virus has at its surface the enzyme neuramidinase, which cleaves N-acetylneuraminic acid moieties from such molecules, eventually destroying their ability to bind the virus. There is, thus, a need for inhibitors of microbial attachment to mammalian cells which have an improved effective lifetime, are readily prepared from inexpensive starting materials and have a broad spectrum of activity.

SUMMARY OF THE INVENTION

The present invention relates to polymers comprising one or more acid-functionalized glycoside moieties which can inhibit or prevent a microbial infection in a mammal, monomers which can serve as starting materials in the synthesis of such polymers, and methods of use of such polymers in the treatment of a microbial infection in a mammal.

The monomers of the present invention include polymerizable monomers comprising an acid-functionalized glycoside moiety. The acid functional group can be, for example, an O-sulfo group or an O-carboxymethyl group. In one embodiment, the monomer has a polymerizable functional group, such as an olefinic bond, to which the acid-functionalized glycoside moiety is attached by a spacer group. The spacer group is, for example, an alkylene group, or an alkylene group wherein one or more carbon atoms are substituted by heteroatoms, such as oxygen, nitrogen or sulfur atoms.

The polymers of the present invention comprise acid-functionalized glycoside moieties, such as pendant acid-functionalized glycoside moieties. Such a polymer can be a homopolymer or a copolymer, and can have, for example, a polyacrylamide, polyacrylate or polystyrene backbone. In one embodiment, the polymer is a copolymer comprising a acid-functionalized glycoside-bearing monomer and acrylamide.

In another embodiment, the present invention includes a method for treating a microbial infection in a mammal, for example, a human, by administering to the mammal a therapeutically effective amount of a polymer comprising one or more acid-functionalized glycoside moieties, such as pendant acid-functionalized glycoside moieties. The acid-functionalized glycoside moieties can be, for example, 3-O-sulfogalactoside moieties or 3-O-carboxymethylgalactoside moieties. The polymer can be a homopolymer or a co-polymer. In one embodiment, the polymer is a copolymer comprising an acid-functionalized glycoside-bearing monomer and acrylamide.

The present invention offers several advantages. It provides agents and a method for the treatment and prevention of microbial infection. In addition the acid-functionalized glycoside-bearing polymers can incorporate a relatively simple and inexpensive sugar.

DETAILED DESCRIPTION OF THE INVENTION

The present invention relates to the incorporation of acid functionalized glycoside moieties into the side chains of synthetic polymers. This provides polyvalent polymers able to bind to a variety of microbes, thereby inhibiting attachment of these microbes to the surfaces of mammalian cells. Such polymers can thus prevent or inhibit a microbial infection in a mammal, such as a human.

The term "acid-functionalized glycoside moiety" as used herein, refers to a glycoside or sugar moiety which is substituted at one hydroxyl oxygen atom with an acidic functional group. Suitable acidic functional groups include the sulfo ($—SO_3H$) group and the carboxymethyl ($—CH_2COOH$) group. The acidic functional group can be protonated or it can be deprotonated to form the conjugate base, an anion which is associated with a counter cation, such as an alkali metal cation, for example a sodium, potassium or cesium ion, or an ammonium or substituted ammonium ion.

One aspect of the present invention includes a polymer comprising one or more acid-functionalized glycoside moieties, wherein the acid functionality is an O-sulfo group or an O-carboxymethyl group. Preferably, the acid-functionalized glycoside moieties are pendant acid-functionalized glycoside moieties.

The term "pendant", as used herein, refers to a structural component of one or more polymer side chains which is not a part of the polymer backbone. Therefore, polymers of the present invention comprise side chains to which are attached acid-functionalized glycoside moieties.

The term "monomer", as used herein, refers to both a molecule comprising one or more polymerizable functional groups prior to polymerization, and a repeating unit of a polymer. A copolymer is said to comprise two or more different monomers. An "acid-functionalized glycoside-bearing monomer" is a monomer, either polymerized or unpolymerized, which comprises an acid-functionalized glycoside moiety. Upon incorporation into a polymer, an acid-functionalized glycoside-bearing monomer comprises a pendant acid-functionalized glycoside moiety.

The present invention includes monomers which are starting materials for the synthesis of polymers which comprise one or more acid-functionalized glycoside moieties, wherein the acid functional group is an O-sulfo group or an O-carboxymethyl group. Such a monomer is linked at the anomeric carbon to a spacer group via an atom, which can be, for example, a carbon atom, or a heteroatom, such as an oxygen, nitrogen or sulfur atom.

In a preferred embodiment, the monomer is of Formula I, $$R_6H_2C \cdots O \cdots Y_y\text{—}X_x\text{—}Z_z\text{—}R \quad (I)$$
$$R_4O \cdots OR_2$$
$$OR_3$$

wherein one of $R_2$, $R_3$, and $R_4$ is —$SO_3H$ or —$CH_2COOH$, the remaining two are each a hydrogen atom, and $R_6$ is a hydrogen atom or a hydroxyl group; or each of $R_2$, $R_3$, and $R_4$ is a hydrogen atom and $R_6$ is —$OSO_3H$ or —$OCH_2COOH$. X is a spacer group and can be a straight chain or branched, substituted or unsubstituted alkylene group wherein, optionally, one or more carbon atoms can be substituted by a heteroatom, such as an oxygen, nitrogen or sulfur atom. Examples include a —$(CH_2)_n$—group, wherein n is an integer from about 2 to about 12, a substituted alkylene group, an oxaalkylene group, such as —$(CH_2)_2O$ $[(CH_2)_2O]_n (CH_2)_2$—, wherein n is an integer from 0 to about 3, or a thiaalkylene group, such as —$(CH_2)_n$ $S(CH_2)_m$—, where n and m are each an integer from 0 to about 10.

The acid-functionalized glycoside moiety can be an α-or β-L-glycoside or an β- or β-D-glycoside moiety. In Formula I, this is indicated by the wavy line connecting Y to the glycoside moiety, which allows for either anomer. The spacer group is attached to the fucoside moiety via Y, which is, for example, a $CH_2$ or NH group, or an oxygen or sulfur atom, and is bonded to the anomeric carbon atom of the glycoside moiety.

The spacer group is attached to the polymerizable olefin unit via Z, which can be, for example, an oxygen atom, a phenylene group, an amidocarbonyl group, an oxycarbonyl group, an amino group or an aminomethylene group. The polymerizable unit can be, for example, an olefinic bond. R is a hydrogen atom or a methyl or ethyl group, and x, y, and z are each, individually, 0 or 1.

The glycoside moiety of Formula I can be derived from, for example, a hexopyranose. Examples of suitable glycoside moieties include fucoside, alloside, altroside, glucoside, mannoside, guloside, idoside, galactoside and taloside moieties. The sulfo or carboxymethyl moiety can be attached to an oxygen atom bonded to any carbon atom other than carbon-1, the anomeric carbon, but is preferably bonded to carbon-3. In a particularly preferred embodiment, the acid-functionalized glycoside moiety is a galactoside moiety to which the acid functionality is attached via the oxygen atom bonded to carbon-3.

A monomer of Formula I can also exist in the conjugate base form. In a conjugate base, the acid functional group is deprotonated, and the monomer carries a net negative charge. A conjugate base of a monomer of Formula I is associated with a counter cation, for example, an alkali metal cation, such as a sodium, potassium or cesium ion, or an ammonium or substituted ammonium ion.

A preferred polymer of the present invention has the general structure:

$$R_6H_2C \cdots O \cdots Y$$
$$R_4O \cdots OR_2$$
$$OR_3$$

wherein the smooth curve represents the polymer backbone and X, Y and Z are as defined above. The acid-functionalized glycoside moiety is linked to a spacer group at the anomeric carbon via Y, which is an oxygen, nitrogen, sulfur or carbon atom. $R_2$, $R_3$, $R_4$ and $R_6$ have the definitions indicated for Formula I, above. The glycoside group can be α- or β-L-glycoside or α- or β-D-glycoside. The spacer group generally has a length ranging from about three to about twelve atoms, which can include, for example, carbon, nitrogen, oxygen and sulfur atoms, and, in a preferred embodiment, terminates in a nitrogen atom which can be, for example, an amide nitrogen of a polyacrylamide backbone. The polymers of the present invention, thus, include homopolymers comprising a monomer of Formula I.

The polymer can also be a copolymer comprising an acid-functionalized glycoside-bearing monomer, for example a monomer of Formula I, and one or more additional monomers which do not bear an acid-functionalized glycoside moiety, such as a neutral hydrophilic monomer. A monomer of this type includes a neutral, polar functional group. Suitable examples include underivatized acrylamide and neutral acrylamide derivatives, such as N-(2-hydroxyethyl) acrylamide. Such a copolymer will preferably comprise a plurality of acid-functionalized glycoside-bearing monomers to enable polyvalent binding to the virus surface. In one example of such a copolymer, the composition of the copolymer can vary substantially, ranging from about 5 mole percent to about 50 mole percent, preferably from about 20 mole percent to about 30 mole percent, of an acid-functionalized glycoside-bearing monomer. The copolymer can, for example, comprise two or more different monomers which are distributed substantially randomly along the polymer chain or can have regions along the polymer chain in which the mole ratio of the monomers is the same as or differs substantially from the mole ratio for the copolymer overall.

In one embodiment a copolymer of the present invention comprises a monomer of Formula I and a hydrophobic monomer. The hydrophobic monomer comprises or is characterized by a hydrophobic moiety, for example, a normal or branched, substituted or unsubstituted $C_3$-$C_{18}$-alkyl group or an aryl or substituted aryl group. Examples of suitable alkyl substituents include halogen atoms, such as fluorine or chlorine atoms and aryl groups, such as a phenyl group. Aryl substituents can include halogen atoms, $C_1$-$C_6$-alkyl groups and $C_1$-$C_6$-alkoxy groups. Suitable hydrophobic monomers include substituted or unsubstituted N-($C_3$-$C_{18}$-alkyl) acrylamides, such as N-n-decylacrylamide and N-isopropylacrylamide. Copolymers comprising a monomer of Formula I and a hydrophobic monomer can further comprise an additional monomer, such as a neutral, hydrophilic monomer. Examples of suitable additional monomers include acrylamide and N-(2-hydroxyethyl)acrylamide.

Polymer backbones which are suitable for the present invention include backbones with low intrinsic toxicity. For example, the polymer can comprise a polyacrylamide, polyacrylate, polystyrene, poly(vinyl alcohol), poly(vinyl amine) or poly(ethyleneimine) backbone. A co-polymer of the present invention can comprise a combination of two or more backbone elements. For example, the copolymer can be a poly(acrylamide-co-styrene) copolymer wherein the acid-functionalized glycoside moiety is attached to either or both of the acrylamide or styrene monomer.

The polymers of use in the present method are preferably substantially nonbiodegradable and nonabsorbable. That is, the polymers do not substantially break down under physiological conditions into fragments which are absorbable by body tissues. The polymers preferably have a nonhydrolyzable backbone, which is substantially inert under conditions encountered in the target region of the body, such as the gastrointestinal tract.

The monomers of the present invention can be prepared by the reaction of acid-functionalized sugars with spacer groups, either before or after attachment of the spacer group to the polymerizable unit. Sulfated glycosides can be prepared, for example, by treatment of the parent sugar with sulfuric acid, chlorosulfuric acid or sulfuryl chloride. These methods, however, generally produce a complex mixture of products. Simple sugars can also be sulfated by reaction with an adduct of sulfur trioxide and a Lewis base such as pyridine or a tertiary amine, provided that all hydroxyl groups other than the desired sulfation site are protected. The selection and use of suitable protective groups for this purpose are well known in the art (see, for example, Greene and Wuts, *Protective Groups in Organic Synthesis*, second edition, N.Y.: Wiley, Chapter 2 (1991)).

A preferred method for synthesizing 3-O-sulfo-β-D-galactose employs the stannylene procedure described by Lubineau et al. (Tet. *Lett.* 35: 8795–8796 (1994)) and Guilbert et al. (Tet.:*Asymmetry* 5: 2163–2178 (1994)). For example, Lubineau et al. reported that p-methoxybenzyl-β-D-galactosyl-2,3-di-O-butylstannylene, formed by the reaction of dibutyltin oxide with p-methoxybenzyl-β-D-galactoside, reacts with sulfur trioxide-trimethylamine to afford p-methoxybenzyl-3-O-sulfo-β-D-galactoside in 81% overall yield. Guilbert et al. reported that treatment of phenyl thio-β-lactoside with dibutyltin oxide followed by reaction with sulfur trioxide-trimethylamine produced the corresponding 3'-O-sulfolactoside in 76% yield.

The polymers of the present invention can be prepared via two general routes, direct polymerization or copolymerization of a monomer bearing an acid-functional glycoside moiety, and nucleophilic side chain substitution on a activated polymer. A homopolymer comprising pendant acid-functionalized glycoside moieties, for example, can be prepared by polymerizing a monomer bearing an acid-functionalized glycoside moiety, such as a monomer of Formula I. A copolymer comprising pendant acid-functionalized glycoside moieties can be prepared by co-polymerizing a mixture comprising an acid-functionalized glycoside-bearing monomer, a second monomer, such as a hydrophobic acrylamide derivative, and, optionally, one or more additional monomers, such as acrylamide and N-(2-hydroxyethyl) acrylamide. The monomers can be polymerized using, for example, methods of free radical polymerization which are well known in the art. Due to reactivity differences between the two monomers, the mole ratio of the monomers in the copolymer product can be different from the mole ratio of the monomers in the initial reaction mixture. This reactivity difference can also result in a non-random distribution of monomers along the polymer chain.

Another synthetic route to polymers comprising pendant acid-functionalized glycoside moieties proceeds via an intermediate polymer comprising labile side chains which are readily substituted by a desired side chain. Suitable polymers of this type include poly(N-acryloyloxy-succinimide) (pNAS), which reacts with a primary amine, for example, to form an N-substituted polyacrylamide. Another suitable polymer with labile side chains is poly(4-nitrophenylacrylate), which also forms an N-substituted polyacrylamide upon reaction with a primary amine or ammonia. This general synthetic approach allows the targeted synthesis of copolymers of widely varying composition.

A co-polymer with a polyacrylamide backbone comprising amide nitrogen atoms substituted with a spacer-acid-functionalized glycoside unit and underivatized amide nitrogen atoms can be prepared by treating pNAS with less than one equivalent (relative to N-acryloyloxysuccinimide monomer) of a primary amine substituted on nitrogen with a spacer group which terminates in a acid-functionalized glycoside moiety. The remaining unreacted N-acryloyloxysuccinimide monomers can then be reacted with ammonia or a second primary amine, to introduce, respectively, underivatized amide groups, or derivatized amide groups with a variety of sizes and polarities. The second amine, for example, can comprise a glycoside moiety, or a hydrophobic or hydrophilic N-substituent. A co-polymer comprising more than two types of acrylamide monomers can be prepared by reacting the activated polymer sequentially with three or more primary amines or ammonia. A variety of copolymer compositions can, thus, be readily obtained by treating the activated polymer with different ratios of the amines.

Another embodiment of the present invention is a method for treating a microbial infection in a mammal, for example, a human, comprising administering to the mammal a therapeutically effective amount of a polymer comprising one or more pendant acid-functionalized glycoside moieties. As used herein, a "therapeutically effective amount" is an amount sufficient to inhibit or prevent (partially or totally) a microbial infection or to reverse development of a microbial infection or prevent or reduce its further progression.

The term "microbial infection", as used herein, refers to the infection of a host organism, such as a mammal, by a pathogenic microbe or microbes, such as bacteria, viruses or protozoa. Microbial infections which can be treated or prevented by the method of the present invention include bacterial infections, such as infection by Streptococcus, including *Streptococcus mutan, Streptococcus salivarius*, and *Streptococcus sanguis*; Salmonella, Campylobacter, including *Campylobacter sputum*; Antinomyces, including *Actinomyces naeslundii* and *Actinomyces viscosus, Escherichia coli, Clostridium difficile*, Staphylococcus, including *S. aureus*; Shigella, Pseudomonas, including *P. aeruginosa; Eikenella corrodens, Actinobacillus actinomycetemcomitans, Bacteroides gingivalis*, Capnocytophaga, including *Capnocytophaga gingivalis; Wolinell recta, Bacteriodes intermedius*, Mycoplasma, including *Mycoplasma salivarium*, Treponema, including *Treponema denticola; Peptostreptococcus micros, Bacteriodes forsythus*, Fusobacteria, including *Fusobacterium nucleatum; Selenomonas sputigena, Bacteriodes fragilis, Enterobacter cloacae* and Pneumocystis. Also included are protozoal infections, such as infection by *Cryptosporidium parvum*, Cyclospora and *Giardia lamblia*; ameobic infections, such as infection by *Entameoba histolytica* or Acanthameoba; fungal infections, such as infections by

*Candida albicans* and *Aspergillus fumigatus*, and parasitic infections, such as infections by *A. castellani* and *Trichinella spiralis*. Viral infections for which the present method is suitable include infections by rotavirus, influenza virus and Norwalk virus. The method is useful for treating infections of various tissues and organs of the body, but is particularly useful for infections of the skin and gastrointestinal tract.

In one embodiment, the polymer to be administered comprises one or more pendant acid-functionalized glycoside moieties. This polymer is, preferably, a polymer of the present invention, as described in detail above. Thus, in a particularly preferred embodiment, the polymer comprises a monomer of Formula I. The polymer can also be a copolymer comprising such a monomer as well as one or more monomers which do not bear a glycoside moiety, such as acrylamide.

The polymer to be administered will, preferably, be of a molecular weight which is suitable for the intended mode of administration and allows the polymer to reach and remain within the targeted region of the body for a period of time sufficient to interact with the infecting organism. For example, a method for treating an intestinal infection should utilize a polymer of sufficiently high molecular weight to resist absorption, partially or completely, from the gastrointestinal tract into other parts of the body. The polymers can have molecular weights ranging from about 500 Daltons to about 500,000 Daltons, preferably from about 2,000 Daltons to about 150,000 Daltons.

The quantity of a given polymer to be administered will be determined on an individual basis and will be determined, at least in part, by consideration of the individual's size, the severity of symptoms to be treated and the result sought. The polymer can be administered alone or in a pharmaceutical composition comprising the polymer, an acceptable carrier or diluent and, optionally, one or more additional drugs.

The polymers can be administered, for example, topically, orally, intranasally, or rectally. The form in which the agent is administered, for example, powder, tablet, capsule, solution, or emulsion, depends in part on the route by which it is administered. The therapeutically effective amount can be administered in a series of doses separated by appropriate time intervals, such as hours.

The invention will now be further and specifically described by the following examples.

EXAMPLES

Example 1

Preparation of 3-Sulfogalactose-acrylamide copolymer

Preparation of tetraacetyl-1-C-allylgalactose, 1

Pentaacetylgalactose (25 g) and allyltrimethylsilane (21 g) were dissolved in acetonitrile (100 mL) at 15° C., to which boron trifluoride-etherate (8 mL) was added dropwise over 5 min. with the temperature of reaction maintained at 15° C. to 20° C. After the addition was complete, the reaction mixture was allowed to room temperature and stirred for 24 hr. The reaction mixture was quenched with saturated aqueous sodium bicarbonate and extracted with diethyl ether. The ether layer was dried over anhydrous sodium sulfate, filtered and the solvent was removed under vacuum to give tetraacetyl-1-C-allylgalactose, 1, (24 g) as a gum.

Preparation of 1-C-allylgalactose, 2

Compound 1 (23 g) was dissolved in 4N NaOH solution (100 mL) and stirred for 2 hr. The reaction mixture was extracted with ether. The aqueous layer was acidified with Dowex-H resin. The resin was removed by filtration and the filtrate was lyophilized to give the deprotected derivative 2 as a white powder. This was recrystallized in ethyl acetate-methanol (7:3) to give crystals (7.0 g). $^1$H NMR (CD$_3$OD): δ 8.2–8.90, m, 1H, CH$_2$C$\underline{H}$=CH$_2$; 5.12–5.09, dd, 2H, CH$_2$CH=C$\underline{H}_2$; 3.99–4.01, m, 1H, H-1; 3.80–3.84, m, 1H, H-2; 3.87–3.62, mm, 3H, H,4,5,6: $^{13}$C NMR (CD$_3$OD): 136.73, 116.86, 75.66, 74.02, 71.91, 70.11, 70.00, 61.97, 31.03: $[\alpha]_D$=+106.45 (c 1.03, methanol).

Preparation of 1-C-allyl-3-sulfo-galactose, 3

Compound 2 (6.8 g) and dibutyltin oxide (8.0 g) were added to a 500 mL RB flask. Anhydrous methanol (100 mL) was then added and the mixture was heated to reflux for 2 hr. The solvent was removed and dried under vacuum for 1 hr. Sulfur trioxide-trimethylamine complex (9 g) was then added, followed by 50 mL anhydrous dioxane. The reaction mixture was stirred for 30 hr at room temperature. The dioxane was removed under vacuum, and the residue was chromatographed on silica gel column using 15% methanol in dichloromethane. 1-C-allyl-3-sulfogalactose, 3, was obtained as white powder (3.92 g). IR: (KBr)/cm$^{-1}$: 3440 (OH), 2855 (CH), 1248 (SO$_3$) : $^1$H NMR (CD$_3$OD): δ, 2.4–2.5, m, 2H, C$\underline{H}_2$CH=CH$_2$; 3.60–3.65, m, 2H, 6-Ha and 6-Hb; 3.7–3.72,m, 1H, H-5; 3.98–4.0, m, 1H, H-1; 4.15–4.2, m, 1H, H-2; 4.28–4.30, m, 1H, H-4; 4.0–4.44,dd, 1H, 3-H; 4.95–5.00, and 5.10–5.15,dd, 2H, CH$_2$CH=C$\underline{H}_2$; 5.75–5.85, m, 1H, CH$_2$C$\underline{H}$=CH$_2$: $^{13}$C NMR (CD$_3$OD): 136.37; 117.02, 79.91, 74.06 (C-3), 68.55, 68.25, 61.67, 45.67, 31.06: $[\alpha]_D$=+60.48 (c 0.62, methanol).

Preparation of 1-C-(6-amino-4-thiahexyl)-3-O-sulfogalactose, HCl salt, 4

Compound 3 (3.8 g), aminoethanethiol.HCl (1.5 g) and 50 mg of azobisisocyanovaleric acid (AICV) were dissolved in 20 mL water in a Pyrex round bottom flask and purged with nitrogen for 10 min. The reaction mixture was irradiated under UV light. After the completion of reaction as judged by TLC, the reaction mixture was passed through a Biogel P2 chromatography column. The appropriate fractions were pooled and lyophilized to give 4 as a glassy material. IR: (KBr)/cm$^{-1}$: 3440 (OH), 2855 (CH), 1250 (SO$_3$). $^1$H NMR (CD$_3$OD): δ,1.6–1.98, m, 6H; 2.72–2.80, m 2H; 2.25–2.35, 2H; 3.79–3.82, m, 2H; 3.9–3.95, m, 1H; 4.39–4.41, m, 1H; 4.5–4.54,dd, 1H: 13C NMR (CD$_3$OD): 77.79 (C-3), 71.52, 66.78, 65.81, 60.35, 44.30, 37.99, 29.95, 27.64, 24.31, 22.36: $[\alpha]_D$=+55.24 (c 0.71, H$_2$O)

Preparation of 1-(6-acrylamido-3-thiahexyl)-3-sulfogalactose, 5

Compound 4 (2.0 g) was dissolved in water/methanol (1:1, 10 mL) to which triethylamine was added to obtain pH 10. N-acryloyloxysuccinimide (1.5 g) was added and stirred for 2h. After TLC analysis indicated the complete disappearance of starting material 4, the volatiles were removed from the reaction mixture. The residue was chromatographed on a silica gel column using 20% methanol in dichloromethane. The appropriate fractions were pooled and solvent was removed to give compound 5 as colorless gum (2.3g). IR: (KBr)/cm$^{-1}$: 3442 2853 (CH), 1259 (SO$_3$) : $^1$H NMR (D$_2$O): δ, 1.6–1.95, mmm, 6H; 2.74–2.80,m 2H; 2.28–2.35, 2H; 3.75–3.81,m, 2H; 3.92–3.95,m, 1H; 4.42–4.44,m, 1H; 4.53–4.59,dd, 1H; 5.83–5.85,dd, 2H, acryloyl CH2; 6.25–6.38,m, 1H, acryloyl CH: $^{13}$C NMR (D$_2$O): 176.95, 168.10, 129.52, 77.83 (C-3), 71.48, 67.08, 66.76, 60.77, 45.30, 38.35, 29.85, 27.94, 24.49, 22.59: $[\alpha]_D$=+ 31.33 (c 0.58, H$_2$O).

Preparation of galactose-3-sulfate (20mol%)-acrylamide (80mol%) copolymer 6

The galactose-3-O-sulfate monomer 5 (2.0 g, 5 mmol) and acrylamide (1.42 g, 20 mmol) were dissolved in 5mL water and purged with nitrogen for 5 min. Radical initiator V-50 (20 mg) was then added and the mixture was heated to 60° C. for 30 min. After the solution became viscous, the heating was discontinued but stirring continued overnight at room temperature. The next day the viscous solution was dialyzed against water using septrapor dialysis bags with a molecular weight cutoff of 3,500 and the dialyzed solution was lyophilized to give the polymer 6 as white powder (2.4 g).

Example 2

Preparation of 3-O-carboxymethylgalactose-acrylamide copolymer

Preparation of 1-C-allyl-3-O-(t-butyloxycarboxy- methyl)galactose 7

Compound 2 (15 g) and dibutyltin oxide (18 g) were refluxed in 100 mL of methanol for 2 hr. The solvent was removed under vacuum and the residue was kept under vacuum for 1 hr at room temperature. Butyl bromoacetate (22 mL) was added to the flask followed by 100 mL anhydrous THF. The mixture was refluxed at 65° C. for 72 hr. TLC analysis indicated the partial formation of the product. The solvent was removed and the residue was purified on silica gel column using 10% methanol in ethyl acetate. Compound 7 was obtained as a colorless gum (8.0 g). IR: (KBr)/cm$^{-1}$: 3420 (OH), 1730, 2862 (CH), : $^1$H NMR (CD$_3$OD) : δ, 1.48, s, 9H, C-(C$\underline{H}_3$)$_3$; 2.41–2.44, 2H; 3.30–3.33,m, 1H; 3.46–3.49,dd, 2H; 3.65–3.69, m, 2H; 3.95–3.99, m, 1H; 4.09–4.15,m, 1H; 4.2–4.24, m, 1H; 4.95–5.00, and 5.10–5.15,dd, 2H, CH$_2$CH=C$\underline{H}_2$; 5.75–5.85, m, 1H, CH$_2$C$\underline{H}$=CH$_2$: $^{13}$C NMR (CD$_3$OD): 173.12, 136.61, 116.89, 83.02, 75, 71, 73.71, 68.75, 67.70, 61.86, 60.96, 30.87, 28.23 (3C): [α]$_D$=+71.07 (C 0.28, methanol).

Preparation of 1-C-allyl-3-O-carboxymethylgalactose, 8

Compound 7 (7.8 g) was dissolved in 2N NaOH solution and stirred for 2 hr. The reaction mixture was acidified with Dowex-H resin and the resin was removed by filtration. The filtrate was lyophilized to give 1-C-allyl-3-O- carboxymethylgalactose (7.0 g). $^1$H NMR (CD$_3$OD) : δ, 2.38–2.42, 2H; 3.28–3.31, m, 1H; 3.44–3.47, dd, 2H; 3.63–3.67,m, 2H; 3.98–4.02, m, 1H; 4.11–4.15,m, 1H; 4.22–4.25,m, 1H; 4.95–5.00, and 5.10–5.15,dd, 2H, CH$_2$CH=C$\underline{H}_2$; 5.75–5.85, m, 1H, CH$_2$C$\underline{H}$=CH$_2$: $^{13}$C NMR (CD$_3$OD) : 176.52 ($\underline{C}$OOH) ; 136.67, 116.89, 81.98, 79.79, 76.00, 73.50, 68.60, 68.56, 67.59, 62.05, 30.70: [α]$_D$=+66.82 (c 0.214, methanol).

Preparation of 1-(6-amino-4-thiahexyl)-3-O-carboxymethylgalactose, 9

Compound 8 (6.2g), 2-aminoethanethiol.HCl (2.7 g) and azobisisocyanovaleric acid (80 mg) were dissolved in water, purged with nitrogen for 10 min. and irradiated under UV light. After 24 hr, the reaction mixture was chromatographed on Biogel-P2 column using water as an eluant. The appropriate fractions were pooled and lyophilized to give the target compound 9 as a colorless foam. $^1$H NMR (D$_2$O) : δ, 1.68–1.98, mm, 6H; 2.65–2.80,m, 2H; 3.05–3.1, m, 2H; 3.32–3.35, m, 1H; 3.7–3.74, dd, 1H; 4.14–4.18, m, 2H; 4.25–4.30, m, 1H; 4.36–4.40, m, 2H: $^{13}$C NMR (D$_2$O) : 175.15 (COOH), 78.86, 74.47, 71.15, 66.78, 66.41, 65.73, 60.82, 38.07, 30.05, 27.72, 24.39, 22.32: [α]$_D$=+57.07 (c 0.21, H$_2$O).

Preparation of 1-C-(6-acrylamido-4-thiahexyl)-3-O-carboxymethylgalactose, 10

Compound 9 (1.5 g) was dissolved in water/methanol (1:1, 10 mL) to which triethylamine was added to obtain pH 10. N-acryloyloxy succinimide (2.0 g) was added and the mixture was stirred for 2 hr. After TLC analysis indicated the complete disappearance of starting material 9, the volatiles were removed from the reaction mixture. The residue was chromatographed on a silica gel column using 20% methanol in dichloromethane. The appropriate fractions were pooled and solvent was removed to give the derivative 10 as a white foam (1.1g). $^1$H NMR (D$_2$O) : δ, 1.62–1.95, mm, 6H; 2.64–2.80, m, 2H; 3.05–3.14, m, 2H; 3.28–3.35, m, 1H; 3.68–3.72, dd, 1H; 4.11–4.15, m, 2H; 4.24–4.29, m, 1H; 4.38–4.41, m, 2H; 5.82–5.86,dd, 2H, acryloyl CH$_2$; 6.26–6.36,m, 1H, acryloyl CH: $^{13}$C NMR (D$_2$O): 176.92, 175.14, 168.12, 129.42, 78.76, 74.44, 71.47, 66.38, 66.41, 65.70, 60.72, 38.21, 30.11, 27.62, 24.49, 22.31.

Preparation of 3-O-carboxymethylgalactose (20 mol%)-acrylamide (80mol%) copolymer, 11

Compound 10 (900 mg, 2.29 mmol) and acrylamide (650mg, 9.16 mmol) were dissolved in 3 mL water and purged with nitrogen for 5 min. Radical initiator V-50 (5 mg) was then added and the mixture was heated to 60° C. for 30 min. After the solution became viscous, the heating was discontinued but stirring continued overnight at room temperature. The next day the viscous solution was poured into isopropanol and the polymer was precipitated. The polymer was collected and dried under vacuum at room temperature. The polymer 11 was obtained as a white powder (820 mg).

Equivalents

Those skilled in the art will recognize or be able to ascertain using no more than routine experimentation many equivalents to the specific embodiments of the invention described herein. Such equivalents are intended to be encompassed in the scope of the following claims.

We claim:

1. A polymer characterized by a polymerized monomer of Formula II,

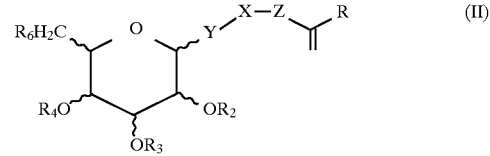

wherein R$_6$ is a hydrogen atom or a hydroxyl group, and one of R$_2$, R$_3$ and R$_4$ is an —SO$_3$H group or a —CH$_2$COOH group or a salt thereof, and the remainder are each a hydrogen atom; or R$_6$ is —OSO$_3$H or —OCH$_2$COOH or a salt thereof and R$_2$, R$_3$ and R$_4$ are each a hydrogen atom; the glycoside moiety is an α- or β-L-glycoside moiety or an α- or β-D-glycoside moiety; X is a straight chain or branched, substituted or unsubstituted alkylene group, wherein, optionally, one or more carbon atoms are substituted by a heteroatom; Y is CH$_2$, NH, an oxygen atom or a sulfur atom; Z is an amidocarbonyl, oxycarbonyl, phenylene, amino, aminomethylene, group, or an oxygen atom; and R is a hydrogen atom or a methyl or ethyl group.

2. A polymer characterized by a polymerized monomer of Formula I,

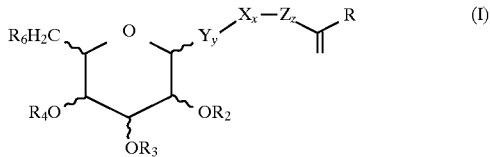

wherein R$_6$ is a hydrogen atom or a hydroxyl group, and one of R$_2$, R$_3$ and R$_4$ is an —SO$_3$H group or a —CH$_2$COOH group or a salt thereof, and the remainder are each a hydrogen atom; or R$_6$ is —OSO$_3$H or —OCH$_2$COOH or a salt thereof and $R_2$, $R_3$ and $R_4$ are each a hydrogen atom; the glycoside moiety is an α- or β-L-glycoside moiety or an α- or β-D-glycoside moiety; X is a straight chain or branched, substituted or unsubstituted alkylene group, wherein, optionally, one or more carbon atoms can be substituted by a heteroatom; Y is $CH_2$, NH, an oxygen atom or a sulfur atom; Z is an amidocarbonyl, oxycarbonyl, phenylene, amino, or aminomethylene group, or an oxygen atom; x, y, and z are each, independently, 0 or 1; and R is a hydrogen atom, a methyl group or an ethyl group.

3. The polymer of claim 1 wherein said polymer is a copolymer.

4. The copolymer of claim 4 further comprising a hydrophobic monomer.

5. The copolymer of claim 4 wherein the hydrophobic monomer comprises a normal or branched $C_3$–$C_{18}$-alkyl group or an aryl group.

6. The copolymer of claim 5 wherein the hydrophobic monomer is an N-($C_3$–$C_{18}$-alkyl)acrylamide.

7. The copolymer of claim 6 wherein the hydrophobic monomer is selected from the group consisting of N-n-decylacrylamide and N-isopropylacrylamide.

8. The copolymer of claim 4 further comprising a neutral hydrophilic monomer.

9. The copolymer of claim 8 wherein the neutral hydrophilic monomer is acrylamide or N-(2-hydroxyethyl) acrylamide.

10. The copolymer of claim 4 comprising from about 20 mole percent to about 30 mole percent of a monomer.

\* \* \* \* \*

UNITED STATES PATENT AND TRADEMARK OFFICE
CERTIFICATE OF CORRECTION

PATENT NO. : 5,821,312
DATED : October 13, 1998
INVENTOR(S) : W. Harry Mandeville, III and Venkata R. Garigapati It is certified that error appears in the above-identified patent and that said Letters Patent is hereby corrected as shown below:

Column 1, before the BACKGROUND OF THE INVENTION, insert the following:

--GOVERNMENT SUPPORT

The invention described herein was supported in whole or in part by Advanced Technology Program Cooperative Agreement No. 70NANB5H1063 from the National Institute of Standards and Technology. The United States Government has certain rights in the invention.--

Signed and Sealed this

Sixth Day of April, 1999

Attest:

Q. TODD DICKINSON

*Attesting Officer*  *Acting Commissioner of Patents and Trademarks*